(12) United States Patent
Lehtola et al.

(10) Patent No.: US 8,642,079 B2
(45) Date of Patent: Feb. 4, 2014

(54) SOLID FORMULATIONS OF OSPEMIFENE

(75) Inventors: Veli-Matti Lehtola, Turku (FI); Kaija Halonen, Rusko (FI)

(73) Assignee: Hormos Medical Corporation, Turku (FI)

( * ) Notice: Subject to any disclaimer, the term of this patent is extended or adjusted under 35 U.S.C. 154(b) by 1468 days.

(21) Appl. No.: 10/783,024

(22) Filed: Feb. 23, 2004

(65) Prior Publication Data
US 2005/0187301 A1   Aug. 25, 2005

(51) Int. Cl.
*A61K 9/20* (2006.01)
(52) U.S. Cl.
USPC ............................................ 424/464; 514/720
(58) Field of Classification Search
None
See application file for complete search history.

(56) References Cited

U.S. PATENT DOCUMENTS

| | | | |
|---|---|---|---|
| 4,117,121 A | 9/1978 | Gallo-Torres | |
| 5,567,714 A | 10/1996 | Bruns | |
| 5,597,582 A | 1/1997 | Brown et al. | |
| 5,912,273 A | 6/1999 | Degregorio et al. | |
| 6,015,544 A | 1/2000 | Foged et al. | |
| 6,037,379 A | 3/2000 | Härkönen et al. | |
| 6,245,352 B1 | 6/2001 | Arbuthnot et al. | |
| 6,245,819 B1 | 6/2001 | Halonen et al. | |
| 6,525,084 B2 | 2/2003 | Rasmussen et al. | |
| 6,984,665 B2 * | 1/2006 | Blom et al. | 514/721 |
| 8,236,861 B2 * | 8/2012 | Anttila | 514/720 |
| 2002/0022649 A1 * | 2/2002 | Rasmussen et al. | 514/422 |
| 2003/0036566 A1 | 2/2003 | Blom et al. | |
| 2003/0055075 A1 * | 3/2003 | Rubsamen | 514/282 |
| 2003/0077297 A1 * | 4/2003 | Chen et al. | 424/400 |
| 2003/0083228 A1 | 5/2003 | Carpino et al. | |
| 2003/0162761 A1 * | 8/2003 | Steiner et al. | 514/186 |
| 2003/0215496 A1 * | 11/2003 | Patel et al. | 424/452 |
| 2005/0187301 A1 | 8/2005 | Lehtola et al. | |
| 2005/0215528 A1 * | 9/2005 | Furuya et al. | 514/89 |
| 2005/0227947 A1 | 10/2005 | Chen et al. | |
| 2006/0105045 A1 | 5/2006 | Buchanan et al. | |
| 2007/0066536 A1 | 3/2007 | Garnick | |

FOREIGN PATENT DOCUMENTS

| | | |
|---|---|---|
| EP | 760 651 | 7/2001 |
| JP | 2003-137814 | 5/2003 |
| WO | WO 96/07402 | 3/1996 |
| WO | WO 97/32574 | 9/1997 |
| WO | WO 02/07718 | 1/2002 |
| WO | WO 03/015820 A1 | 2/2003 |
| WO | WO 03/103649 | 12/2003 |

OTHER PUBLICATIONS

V. Craig Jordan, "Antiestrogens and Selective Estrogen Receptor Modulators as Multifunctional Medicines, 2. Clinical Considerations and New Agents," Journal of Medicinal Chemistry, vol. 46, No. 7, Mar. 27, 2003, pp. 1081-1111.

Lauri Kangas, "Biochemical and pharmacological effects of toremifene metabolites," Cancer Chemother. Pharmacol. vol. 27, Apr. 1990, pp. 8-12.
Rudnic, E.M., "Oral Solid Dosage Forms", Remington: The Science and Practice of Pharmacy, Gennaro, A.R., editor, 20th Ed. Chapter 45, pp. 858-871.
Chueschov, "Industrial technology of drugs", 353-355 (1999). (with translation).
BI Dianzhou, Chinese Textbook, Pharmaceutics, Fourth Edition (2003), People's Medical Publishing House. (with translation).
S.K. Voipio, et al., "Effects of ospemifene (FC-1271a) on uterine endometrium, vaginal maturation index, and hormonal status in healthy postmenopausal women." *Maturitas* vol. 43, 204-214 (2002).
Raymond F. Kauffman, et al., "Selective Estrogen Receptor Modulators," Drug News & Perspectives 1995 8 (9) pp. 531-539.
Christopher J.H. Porter, et al., "Lipid Based Formulations For Oral Administration," Journal of Receptor & Signal Transduction Research, 21 (2&3) 215-257 (2001).
Odeku Oluwatoyin A., Fell, John T.; *Effects of the method of preparation on the compression, mechanical, and release properties of Khaya gum matrices*; Pharmaceutical development and technology; 2006; vol. 11; No. 4, pp. 435-441.
International Preliminary Report on Patentability and Written Opinion for PCT/FI2005/000037, dated May 23, 2006 (received Jun. 13, 2006).
International Search Report of PCT/FI2005/000037, dated May 24, 2005.
International Preliminary Report on Patentability and Written Opinion for PCT/2005/000131, dated Nov. 7, 2006.
International Search Report of PCT/FI2005/000131, dated Jun. 20, 2005.
European Patent Office Examination Reports for Application No. 05 708 125.9 (PCT/FI2005/000037), dated Sep. 26, 2008.
European Patent Office Examination Reports for Application No. 05 708 125.9 (PCT/FI2005/000037), dated Mar. 25, 2008.

(Continued)

*Primary Examiner* — Hasan Ahmed
(74) *Attorney, Agent, or Firm* — Brinks Gilson & Lione; Ryan L. Marshall; William Boudreaux

(57) ABSTRACT

This invention relates to a solid drug formulation comprising granulates containing a therapeutically active compound of the formula (I)

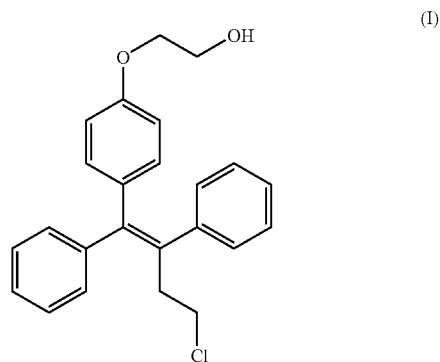

or a geometric isomer, a stereoisomer, a pharmaceutically acceptable salt, an ester thereof or a metabolite thereof, in combination with one or more intra-granular excipients.

18 Claims, 1 Drawing Sheet

(56) References Cited

OTHER PUBLICATIONS

European Patent Office Examination Reports for Application No. 05 708 125.9 (PCT/FI2005/000037), dated Jul. 20, 2007.
European Patent Office Examination Reports for Application No. 05 717 258.7 (PCT/2005/000131), dated May 5, 2009.
European Patent Office Examination Reports for Application No. 05 717 258.7 (PCT/2005/000131), dated Nov. 9, 2007.
Patent Office of the Russian Federation, Official Action for Application No. 2006133902 with English translation, dated Jan. 26, 2009.
Patent Office of the Russian Federation, Official Action for Application No. 2006133902 with English translation, dated Dec. 14, 2009.
Chinese Patent Office, Office Action for Application No. 200580004972.7 (PCT/FI2005/000037) with English translation, dated Jan. 9, 2009.
G.K. Bolhuis, K. Zuurman, G.H.P. te Wierik; Improvement of dissolution of poorly soluble drugs by solid deposition on a super disintegant. II. The choice of super disintegrants and effect of granulation; European Journal of Pharmaceutical Sciences; 1997; 63-69; Elsevier Science B.V.
SJ Laight, PCM Mossop, MC Wilkinson; Comparative evaluation of two aspirin formulation techniques; www.ru.ac.za/academic.departments/pharmacy/jrats/vol1_1/poster5/tablet2.html; printed Dec. 3, 2007; 1-6.
Quinton Singh, Hiren Patel, Mohamed Cassim; Comparative Evaluations of Tablet Formulations; Rhodes University, School of Pharmaceutical Sciences, Department of Pharmaceutics, Rhodes University, Grahamstown, 6140, RSA; www.ru.ac.za/academic/departments/pharmacy/jrats/vol1_1/poster6/tablet8.html; printed Dec. 3, 2007; 1-6.
Odeku Oluwatoyin A., Fell, John T.; Effects of the method of preparation on the compression, mechanical, and release properties of Khaya gum matrices; Pharmacautical development and technology; 2006; vol. 11; 435-411.

* cited by examiner

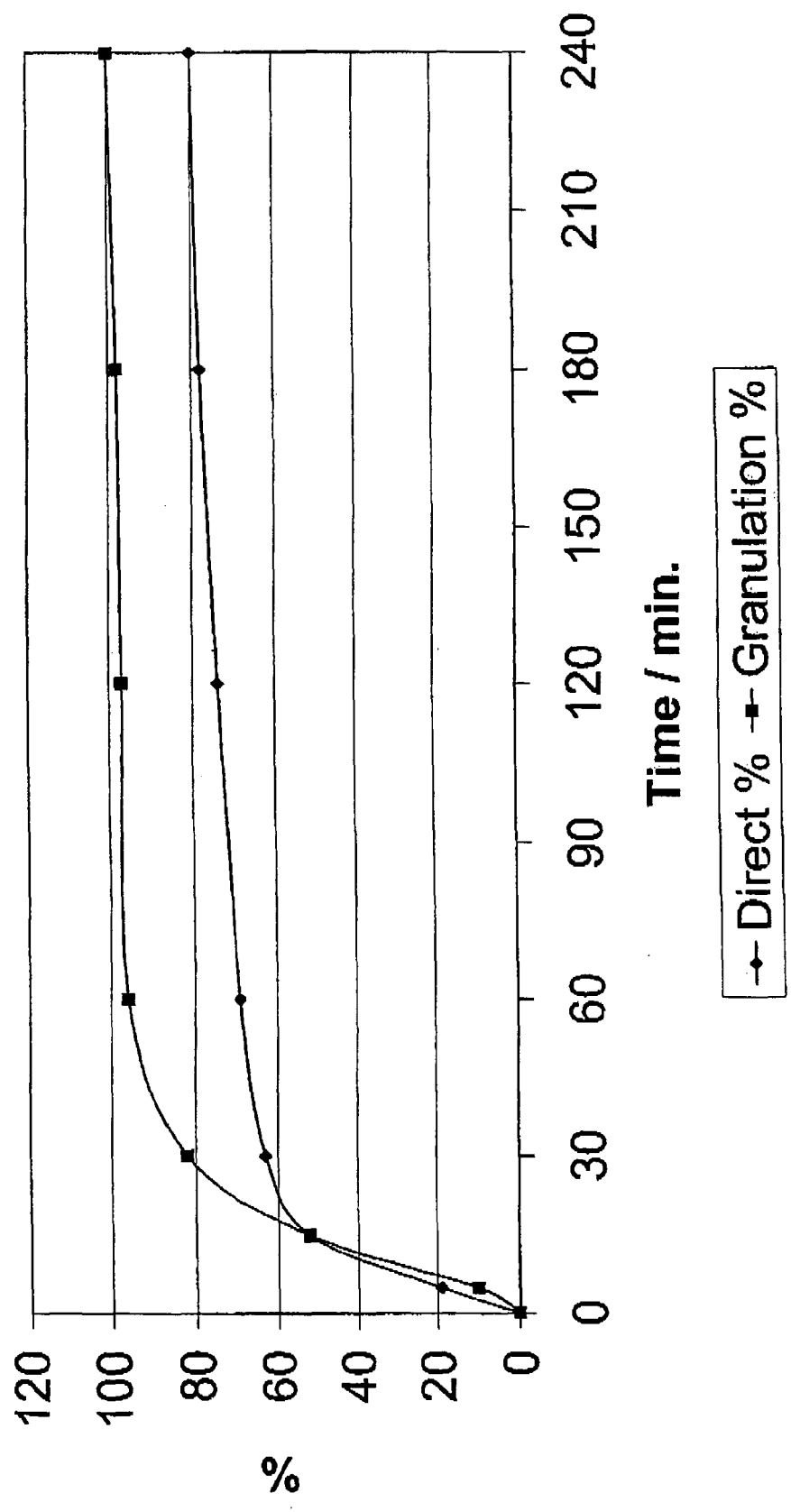

SOLID FORMULATIONS OF OSPEMIFENE

FIELD OF THE INVENTION

This invention relates to a solid drug formulation comprising granulates containing ospemifene or a closely related compound.

BACKGROUND OF THE INVENTION

The publications and other materials used herein to illuminate the background of the invention, and in particular, cases to provide additional details respecting the practice, are incorporated by reference.

"SERM"s (selective estrogen receptor modulators) have both estrogen-like and antiestrogenic properties (Kauffman & Bryant, 1995). The effects may be tissue-specific as in the case of tamoxifen and toremifene which have estrogen-like effects in the bone, partial estrogen-like effect in the uterus and liver, and pure antiestrogenic effect in breast cancer. Raloxifene and droloxifen are similar to tamoxifen and toremifene, except that their antiestrogenic properties dominate. Based on the published information, many SERMs are more likely to cause menopausal symptoms than to prevent them. They have, however, other important benefits in elderly women: they decrease total and LDL cholesterol, thus deminishing the risk of cardiovascular diseases, and they may prevent osteoporosis and inhibit breast cancer growth in postmenopausal women. There are also almost pure antiestrogens under development.

Ospemifene is the Z-isomer of the compound of formula (I)

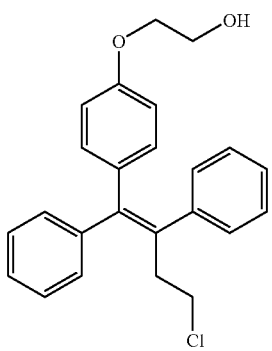

(I)

and it is one of the main metabolites of toremifene, is known to be an estrogen agonist and antagonist (Kangas, 1990; International patent publications WO 96/07402 and WO 97/32574). The compound is also called (deaminohydroxy) toremifene and it is also known under the code FC-1271a. Ospemifene has relatively weak estrogenic and antiestrogenic effects in the classical hormonal tests (Kangas, 1990). It has anti-osteoporosis actions and it decreases total and LDL cholesterol levels in both experimental models and in human volunteers (International patent publications WO 96/07402 and WO 97/32574). It also has antitumor activity in an early stage of breast cancer development in an animal breast cancer model. Ospemifene is also the first SERM which has been shown to have beneficial effects in climacteric syndromes in healthy women. The use of ospemifene for the treatment of certain climacteric disorders in postmenopausal women, namely vaginal dryness and sexual dysfunction, is disclosed in WO 02/07718. The published patent application WO 03/103649 describes the use of ospemifene for inhibition of atrophy and for the treatment or prevention of atrophy-related diseases or disorders in women, especially in women during or after the menopause.

OBJECT AND SUMMARY OF THE INVENTION

An object of the present invention is to provide an improved solid drug formulation containing ospemifene, where the dissolution of the drug is essentially increased.

Thus, the invention concerns a solid drug formulation comprising granulates containing a therapeutically active compound of the formula (I)

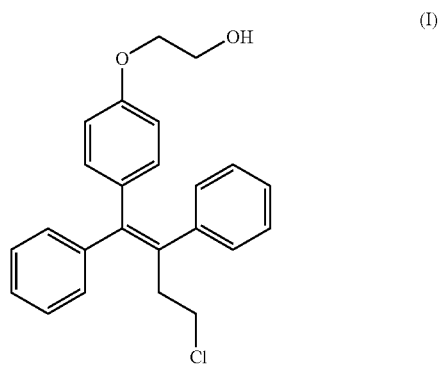 [SMILES: OCCOc1ccc(/C(=C(/CCCl)c2ccccc2)c2ccccc2)cc1]

(I)

or a geometric isomer, a stereoisomer, a pharmaceutically acceptable salt, an ester thereof or a metabolite thereof, in combination with one or more intra-granular excipients.

BRIEF DESCRIPTION OF THE DRAWING

FIG. 1 shows dissolution versus time for ospemifene from tablets made by direct compression of the ingredients (diamonds) and from tablets made from granulates comprising the drug (squares).

DETAILED DESCRIPTION OF THE INVENTION

Granulation: Granulation is a process where primary powder particles are made to adhere to form larger, multiparticle entities called granules. Pharmaceutical granules typically have a size range between 0.2 and 4.0 mm, depending on their subsequent use. In the majority of cases this will be in the production of tablets or capsules when granules will be made as an intermediate product and will have a typical size range between 0.2 and 0.5 mm.

The main reasons for granulation are:

Prevention of segregation of the constituents of the powder mix. Segregation or demixing is primarily due to differences in the size or density of the components of the mix, the smaller and/or denser particles concentrating at the base or a container with the larger and/or less dense ones above them. An ideal granulation will contain all the constituents of the mix in the correct proportion in each granule and segregation of the ingredients will not occur.

Improving the flow properties of the mix. Many powders, because of their small particle size, irregular shape or surface characteristics, are cohesive and do not flow well. Poor flow will often result in a wide weight variation within the final product owing to variable fill of tablet dies etc.

Improving the compaction characteristics of the mix. Some powders are difficult to compact even it a readily compactable adhesive is included in the mix, but granules of the same formulation are often more easily compacted and produce stronger tablets.

Also other reasons can be mentioned: reduction of dust when handling powders, avoid adhering of slightly hygroscopic materials when stored.

The granulation methods can be divided in two types: wet granulation and dry granulation. In a suitable formulation a number of different excipients will be needed in addition to the drug. The common types are diluents, to produce a unit dose weight of a suitable size, and disintegrating agents, which are added to aid the break-up of the granule when it reaches a liquid medium, e.g. on ingestion by the patient. Adhesives in the form of a dry powder may also be added, particularly if dry granulation is employed. These ingredients will be mixed before granulation.

Excipients in the granulates are also called intra-granular excipients. When the granulates are formulated to the final formulations, excipients will be added. Excipients outside the granulates are called extra-granular excipients.

In the dry granulation methods the primary powder particles are aggregated under high pressure. There are two main processes: either a large tablet (slug) is produced in a heavy-duty tabulating press, or the powder is squeezed between two rollers to produce a sheet of material (roller compaction).These intermediate products are broken by a suitable milling technique. The dry granulation is used for drugs which are sensitive to moisture.

The wet granulation involves the massing of a mix of dry primary powder particles using a granulating fluid. The fluid contains a solvent which must be non-toxic and volatile so that it can be removed by drying. Typical liquids include water, ethanol, and isopropanol, either alone or in combination. The granulation liquid may be used alone or, more usually, as a solvent containing a dissolved adhesive (binding agent) which is used to ensure particle adhesion once the granule is dry. The wet mass is forced through a sieve to produce wet granules which are then dried. A subsequent screening stage breaks agglomerates and removes the fine material.

Dissolution testing: In vitro dissolution testing serves as an important tool for characterizing the biopharmaceutical quality of a product at different stages in its lifecycle. In early drug development in vitro dissolution properties are supportive for choosing between different alternative formulation candidates for further development and for evaluation of active ingredients/drug substances. Moreover, in vitro dissolution data will be of great importance when assessing changes in production site, manufacturing process or formulation and assist in decision concerning the need for bioavailability studies.

Drug absorption from a solid dosage form after oral administration depends on the release of the drug substance from the drug product, the dissolution or solubilization of the drug under physiological conditions, and the permeability across the gastrointestinal tract. Because of the critical nature of the first two of these steps, in vitro dissolution may be relevant to the prediction of in vivo performance. Based on this general consideration, in vitro dissolution tests for immediate release solid oral dosage forms, such as tablets and capsules, are used to a) assess the lot-to-lot quality of a drug product; b) guide development of new formulations; and c) ensure continuing product quality and performance after certain changes, such as changes in the formulation, manufacturing process, site of manufacture, and the scale-up of a manufacturing process.

Dissolution profile comparisons: Dissolution profiles may be considered similar by virtue of 1) overall profile similarity and 2) similarity at every dissolution sample time point. The dissolution profile comparisons may be carried out using model independent or model dependent methods.

The similarity factor $f_2$ is a logarithmic reciprocal square root transformation of the sum of squared error and is a measurement of the similarity in the percent (%) dissolution between two curves. The similarity factor is calculated according to the following formula $$f_2 = 50 \cdot \log\left(100 \div \sqrt{1 + (1/n) \cdot \left(\sum_{t=1}^{n}(R_t - T_t)(R_t - T_t)\right)}\right)$$

where n is the number of sampling timepoints; $R_t$ is the amount drug released from a reference batch at time t and $T_t$ is the amount drug released from a test batch at time t. For curves to be considered similar, $f_2$ should be close to 100. Generally, $f_2$ values greater than 50 ensure sameness or equivalence of the two curves, i.e. sameness of the performance of the reference product and test product.

In the drug formulation according to this invention, the intra-granular excipient can be composed of one or more ingredients, which may belong to the same or different categories of excipients. At least one intra-granular excipient is a disintegrant or a mixture of several disintegrants; a diluent or a mixture of several diluents; or a binder or a mixture of several binders. The intra-granular excipient may also be a combination of at least one diluent and at least one binder; a combination at least one diluent and at least one disintegrant; a combination of at least one disintegrant and at least one binder; or a combination of at least one diluent, at least one disintegrant and at least one binder.

As typical non-limiting examples of suitable disintegrants can be mentioned povidone, crospovidone, carboxymethylcellulose, methylcellulose, alginic acid, croscarmellose sodium, sodium starch glycolate, starch, formaldehyde-casein or their combinations.

As typical non-limiting examples of suitable diluents can be mentioned maltose, maltodextrin, lactose, fructose, dextrin, microcrystalline cellulose, pregelatinized starch, sorbitol, sucrose, silicified microcrystalline cellulose, powdered cellulose, dextrates, mannitol, calsium phospate or combinations thereof.

As typical non-limiting examples of suitable binders can be mentioned acacia, dextrin, starch, povidone, carboxymethylcellulose, guar gum, glucose, hydroxypropyl methylcellulose, methylcellulose, polymethacrylates, maltodextrin, hydroxyethyl cellulose or combinations thereof.

The granulates can be made either by dry granulation or by wet granulation according to known technology. Suitable solvents in wet granulation are e.g. water or ethanol.

The final solid drug formulation can be any suitable solid formulation such as tablets, capsules, granulates as such or granulates packaged into suitable dosage units, caplets, lozenges, and the like. The term "tablet" shall be understood to cover any kind of tablets, such as uncoated tablets, coated tablets, film-coated tablets, effervescent tablets, oral lyophilisates, orodispersable tablets, gastro-resistant tablets, prolonged-release tablets, modified-release tablets, chewable tablet, oral gums and pillules. The granulates shall be understood to cover also effervescent, gastro-resistant, prolonged-release and modified-release granulates. The capsule shall also be understood to cover gastro-resistant, prolonged-release and modified-release capsules.

The formulation may for example be a capsule comprising the granulates encapsulated in a shell made of gelatine or the like. The formulation can in addition to the granulates comprise an extra-granular lubricant. A typical lubricant is, for example, calcium stearate, magnesium stearate, stearic acid, talc, a vegetable oil, poloxamer, a mineral oil, sodium lauryl sulphate, sodium stearyl fumarate, zinc stearate or combinations thereof The formulation can also contain other extra-granular excipients, for example diluents.

The drug formulation may alternatively be a tablet comprising the granulates in combination with one or more extra-granular excipient. The extra-granular excipient can be one or more disintegrants, one or more diluents, one or more binders, one or more lubricants, or their combinations. The extra-granular disintegrant can be one of the disintegrants mentioned above or combinations thereof. Similarly, the extra-granular diluents, binders, and lubricants can be selected from those mentioned before.

The tablet can also comprise other extra-granular ingredients such as flavouring agents, colouring agents, preservatives, suspending aids and fillers.

The granulates comprise preferably one or more disintegrants in the range 0.1 to 10, preferably 0.1 to 4 weight-% of the granulates and one or more diluents in the range 20 to 80 weight-% of the granulates.

If the granulates are processed into tablets, such tablets may contain, e.g. extra-granular disintegrants in the range 0.1 to 25%, lubricants 0.1 to 2%, drug containing granulates in the range 20 to 80%, and the remaining part diluents optionally in combination with other other ingredients such as binders, flavouring agents, colouring agents, preservatives, suspending aids, fillers and the like. The percentages are all weight-% of the tablet.

The improved drug formulation according to this invention is particularly useful when treating women during or after the menopause. However, the method according to this invention is not restricted to women in this age group.

The term "metabolite" shall be understood to cover any ospemifene or (deaminohydroxy)toremifene metabolite already discovered or to be discovered. As examples of such metabolites can be mentioned the oxidation metabolites mentioned in Kangas (1990) on page 9 (TORE VI, TORE VII, TORE XVIII, TORE VIII, TORE XIII), especially TORE VI and TORE XVIII, and other metabolites of the compound. The most important metabolite of ospemifene 4-hydroxy-ospemifene, which has the formula

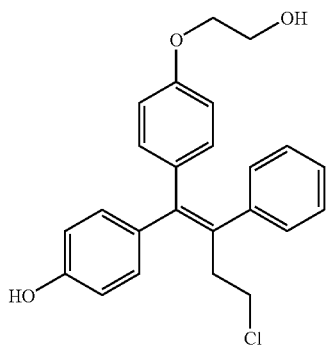 [SMILES: OCCOc1ccc(/C(=C(/CCCl)c2ccccc2)c2ccc(O)cc2)cc1]

The use of mixtures of isomers of compound (I) shall also be included in this invention.

The compound (I) is preferably ospemifene.

The particle size of the ospemifene in the granulates is important in order to get a good dissolution. Preferably at least 90% of the drug substance shall have a particle size less than 250 micrometer. More preferably, 90% of the drug substance shall have a particle size less than 150 micrometer, and 50% of the drug substance shall have a particle size less than 25 micrometer. Especially preferably, 90% of the drug substance shall have a particle size less than 50 micrometer, and 50% of the drug substance shall have a particle size less than 15 micrometer.

The term "particle size" refers to the particle diameter, or in case the particles are not spherical, to the largest extension in one direction of the particle.

The improved drug formulation according to this invention is useful in any application of ospemifene, especially when the compound is used for treatment or prevention of osteoporosis or for treatment or prevention of symptoms related to skin atrophy, or to epithelial or mucosal atrophy.

A particular form of atrophy which can be inhibited by administering of ospemifene is urogenital atrophy. Symptoms related to urogenital atrophy can be divided in two subgroups: urinary symptoms and vaginal symptoms. As examples of urinary symptoms can be mentioned micturation disorders, dysuria, hematuria, urinary frequency, sensation of urgency, urinary tract infections, urinary tract inflammation, nocturia, urinary incontinence, urge incontinence and involuntary urinary leakage.

As examples of vaginal symptoms can be mentioned irritation, itching, burning, maladorous discharge, infection, leukorrhea, vulvar pruritus, feeling of pressure and postcoital bleeding.

According to previous data, the optimal clinical dose of ospemifene is expected to be higher than 25 mg daily and lower than 100 mg daily. A particularly preferable daily dose has been suggested in the range 30 to 90 mg. At the higher doses (100 and 200 mg daily), ospemifene shows properties more similar to those of tamoxifen and toremifene. Due to the enhanced bioavailability according to the method of this invention, it can be predicted that the same therapeutical effect can be achieved with doses lower those recommended earlier.

The invention will be disclosed more in detail in the following non-restrictive Experimental Section.

Experimental Section

Two different ospemifene tablets were made. One of them was made of ospemifine granulates, which were made by the wet method, and the other tablet was made by direct compression of the ingredients.

The composition of the two tablets is given below.

| Names of the ingredients | Quantity (%) GRANULATION | Quantity (%) DIRECT COMPRESSION | Function |
| --- | --- | --- | --- |
| Ospemifene | 30 | 30 | Active |
| Pregelatinized starch | 38 | 38 | Diluent |
| Maize starch | 25 | 25 | Diluent |
| Povidone | 2 | 2 | Binder |
| Sodium starch glycolate | 4 | 4 | Disintegrant |
| Magnesium stearate | 1 | 1 | Lubricant |
| Water, purified* | 25 | — | Solvent |

*Evaporates during the manufacturing process

The tablets were subjected to dissolution testing according to the USP 24 paddle method using manual sampling. One tablet was paced in each of twelve vessels containing 900 ml of 2% sodium dodecyl sulphate. The pH was 9.8. After 5, 15, 30, 60, 120, 180, 210, and 240 minutes, 10 ml was manually withdrawn from the dissolution vessels. The samples were filtered immediately and spectrophotometrically analysed using a 2-mm flow-through cell in a computerized spectrophotometer. The concentration of ospemifene in the sample solution was determined by comparison of the absorbance at 238 nm with that of a standard solution. The results are shown in FIG. 1. The calculated similarity factor $f_2$ was 36, which means that the dissolution profiles for the two tablets are very different.

FIG. 1 shows that the tablet containing granulates significantly improves the dissolution of ospemifene, compared to tablets manufactured by direct compression.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

Kangas L. Biochemical and pharmacological effects of toremifene metabolites. Cancer Chemother Pharmacol 27:8-12, 1990.

Kauffinan R F, Bryant H U. Selective estrogen receptor modulators. Drug News Perspect 8: 531-539, 1995.

The invention claimed is:

1. A solid drug formulation comprising granulates containing 30 to 90 mg of ospemifene or a pharmaceutically acceptable salt thereof, in combination with one or more intra-granular excipients selected from a disintegrant, a diluent, a binder, and combinations of the same;
wherein 90% of the ospemifene or the pharmaceutically acceptable salt thereof has a particle size less than 50 micrometers and 50% of the ospemifene or the pharmaceutically acceptable salt thereof has a particle size less than 15 micrometers.

2. The drug formulation according to claim 1 wherein the active ingredient is ospemifene.

3. The drug formulation according to claim 1 wherein the disintegrant is selected from the group consisting of povidone, crospovidone, carboxymethyl-cellulose, methylcellulose, alginic acid, croscarmellose sodium, sodium starch glycolate, starch, formaldehyde-casein and combinations thereof.

4. The drug formulation according to claim 1 wherein at least one intra-granular excipient is a diluent.

5. The drug formulation according to claim 1 wherein at least one intra-granular excipient is a binder.

6. The drug formulation according to claim 1 wherein the intra-granular excipient is selected from:
a combination of at least one diluent and at least one disintegrant;
a combination of at least one disintegrant and at least one binder; or
a combination of at least one diluent, at least one disintegrant and at least one binder.

7. The drug formulation according to claim 4 wherein the diluent is selected from the group consisting of maltose, maltodextrin, lactose, fructose, dextrin, microcrystalline cellulose, pregelatinized starch, sorbitol, sucrose, silicified microcrystalline cellulose, powdered cellulose, dextrates, mannitol, calcium phosphate and combinations thereof.

8. The drug formulation according to claim 5 wherein the binder is selected from a group consisting of acacia, dextrin, starch, povidone, carboxymethylcellulose, guar gum, glucose, hydroxypropyl methylcellulose, methylcellulose, polymethacrylates, maltodextrin, hydroxyethyl cellulose and combinations thereof.

9. The drug formulation according to claim 1 wherein the granulates are made by wet granulation.

10. The drug formulation according to claim 2 wherein the disintegrant is selected from the group consisting of povidone, crospovidone, carboxymethyl-cellulose, methylcellulose, alginic acid, croscarmellose sodium, sodium starch glycolate, starch, formaldehyde-casein and combinations thereof.

11. The drug formulation according to claim 2 wherein the intra-granular excipient is selected from:
a combination at least one diluent and at least one disintegrant;
a combination of at least one disintegrant and at least one binder; or
a combination of at least one diluent, at least one disintegrant and at least one binder.

12. The drug formulation according to claim 11 wherein the diluent is selected from the group consisting of maltose, maltodextrin, lactose, fructose, dextrin, microcrystalline cellulose, pregelatinized starch, sorbitol, sucrose, silicified microcrystalline cellulose, powdered cellulose, dextrates, mannitol, calcium phosphate and combinations thereof.

13. The drug formulation according to claim 12 wherein the binder is selected from a group consisting of acacia, dextrin, starch, povidone, carboxymethylcellulose, guar gum, glucose, hydroxypropyl methylcellulose, methylcellulose, polymethacrylates, maltodextrin, hydroxyethyl cellulose and combinations thereof.

14. A solid drug formulation comprising granulates containing 30 to 90 mg of ospemifene or a pharmaceutically acceptable salt thereof in combination with one or more intra-granular excipients selected from pregelatinized starch, maize starch, povidone, sodium starch glycolate, and magnesium stearate, wherein at least 80% of the formulation is dissolved within 30 minutes after subjecting said formulation to dissolution testing at pH 9.8 according to the USP 24 paddle method;
wherein 90% of the ospemifene or the pharmaceutically acceptable salt thereof has a particle size less than 50 micrometers and 50% of the ospemifene or the pharmaceutically acceptable salt thereof has a particle size less than 15 micrometers.

15. The drug formulation according to claim 1 wherein the disintegrant is sodium starch glycolate.

16. The drug formulation according to claim 2 wherein the disintegrant is sodium starch glycolate.

17. The drug formulation according to claim 1 wherein the disintegrant is in the range of 0.1 to 10 weight % of the granulates and wherein at least 80% of the formulation is dissolved within 30 minutes after subjecting said formulation to dissolution testing at pH 9.8 according to the USP 24 paddle method.

18. The drug formulation according to claim 6, wherein the at least one diluent comprises pregelatinized starch, the at least one disintegrant comprises sodium starch glycolate, and the at least one binder comprises povidone.

* * * * *